US008099306B2

(12) United States Patent
Ruben et al.

(10) Patent No.: US 8,099,306 B2
(45) Date of Patent: Jan. 17, 2012

(54) PHARMACY EPISODES OF CARE

(75) Inventors: Manon S. Ruben, Lebanon, NH (US); Richard Lieberman, Baltimore, MD (US)

(73) Assignee: The TriZetto Group, Inc., Greenwood Village, CO (US)

( * ) Notice: Subject to any disclaimer, the term of this patent is extended or adjusted under 35 U.S.C. 154(b) by 601 days.

(21) Appl. No.: 12/027,095

(22) Filed: Feb. 6, 2008

(65) Prior Publication Data

US 2009/0198517 A1   Aug. 6, 2009

(51) Int. Cl.
G06F 19/00 (2011.01)
(52) U.S. Cl. ............................................... 705/3
(58) Field of Classification Search .................. 705/2, 3, 705/400
See application file for complete search history.

(56) References Cited

U.S. PATENT DOCUMENTS

| | | | |
|---|---|---|---|
| 5,557,514 | A | 9/1996 | Seare et al. |
| 5,918,208 | A | 6/1999 | Javitt |
| 5,970,463 | A * | 10/1999 | Cave et al. ......................... 705/3 |
| 6,223,164 | B1 | 4/2001 | Seare et al. |
| 6,370,511 | B1 | 4/2002 | Dang |
| 7,222,079 | B1 | 5/2007 | Seare et al. |
| 2003/0167189 | A1 | 9/2003 | Lutgen et al. |
| 2004/0039710 | A1* | 2/2004 | McMillan et al. ............. 705/400 |
| 2005/0144038 | A1* | 6/2005 | Tamblyn et al. .................. 705/2 |
| 2007/0005402 | A1 | 1/2007 | Kennedy et al. |

OTHER PUBLICATIONS

International Search Report and the Written Opinion issued for PCT/US2009/33428, dated Mar. 13, 2009, 8 pages.
Weiner, Jonathan P., "Maximizing the Use of Pharmacy Data for a Medicare Population" Copyright 2007—John Hopkins University, pp. 1-43.

* cited by examiner

Primary Examiner — Gerald J. O'Connor
Assistant Examiner — John Pauls
(74) Attorney, Agent, or Firm — Dawn-Marie Bey; King & Spalding LLP (57) ABSTRACT

A computer-implemented method for grouping, categorizing, and profiling pharmaceutical claims data to assist health care managers in determining (a) medication treatment experience, outcomes, and medication compliance behaviors of patients and (b) appropriate drug prescribing, medication coordination, and cost-efficiency of health care providers. An objective means is provided for categorizing and quantifying patterns of prescription drug utilization as a health care service within a clinically relevant time frame. A pharmacy episode group (PEG) is a pharmacologically homogenous grouping of drugs with the same therapeutic ingredients used by a patient once or over an extended period of time. The PEG is a patient-centered pharmacy classification unit, which uses script-level pharmacy claim data as input data and assigns each script to the appropriate episode. Pharmacy episodes are categorized based on algorithms linking the pattern of a physician's recommended use (drug supply) and the patient's pattern of compliance (intervals between fill dates). The system also identifies multi-drug and concurrent use drug episodes, flags patients' records where intervals between scripts suggest non-compliance with recommended therapy, selects the most recent claims, resets windows (episode start and end dates), and ultimately assigns all pharmacy claims to episodes.

9 Claims, 4 Drawing Sheets

| PRESCRIPTION ID | EPISODE TYPE | FILL DATE | SUPPLY | DRUG STATUS |
|---|---|---|---|---|
| 40-1 { 001-01<br>001-02<br>001-03 | ME-01 | 01 01 2006<br>03 17 2006<br>06 01 2006 | 90<br>90<br>90 | CC1 |
| 40-2 { 002-01<br>002-02 | EI-01 | 01 01 2006<br>02 10 2006 | 30 | CC1 |
| 40-3 { 003-01 | AI-01 | ... | ... | ... |
| ... | | | | |
| 40-N { 00N-01<br>00N-02<br>00N-03 | AI-0N | | | |

PHARMACY EPISODES OF CARE

TECHNICAL FIELD

The following description relates generally to computer-implemented methods for processing pharmaceutical claims for informational content, rather than for payment. More particularly, the description relates to a computer-implemented method for receiving input data relating to a person's claims for prescription drugs, establishing a pharmaceutical event record for the person, establishing pharmacy episode groupings of data records of related medication management patterns, correlating subsequent pharmaceutical claims events to a pharmacy episode category and manipulating pharmacy episode categories based upon time windows relating to physician's use instructions, multi-drug therapeutic strategy, concurrent drug use, and patient's patterns of compliance with physician-indicated use of the drug(s). In certain embodiments, a Pharmacy Episode Grouping System (PEGS) has logically consistent non-disease based rules for episode boundaries (start and end dates) and its methodology for episode creation is valid and consistent, regardless of medical condition, treatment setting, or drug type.

BACKGROUND OF THE INVENTION

The third-party payer healthcare industry is a well-established industry. In general, in such third-party payer health care industry, a "third party" (referred to herein generally as an "insurer") pays for healthcare services received from a service provider (any person, such as a doctor, nurse, dentist, optometrist, pharmacist, etc., or institution, such as a hospital, clinic, or medical equipment provider, that provides medical care, services, drugs, healthcare supplies, medical equipment, home health, etc.) to a member (or "insured") consumer. As used herein, a healthcare consumer is any person to whom healthcare services are rendered. In some situations, the healthcare consumer may be referred to herein as a "patient", but the services rendered are not limited to those rendered by a physician and thus "healthcare consumer" is not limited to a patient. The healthcare consumer may also be referred to herein as a "member" because the consumer is a member of one or more healthcare plans under which a third-party payer (insurer) pays for at least a portion of certain healthcare services rendered to the consumer.

Examples of third-party payers (or "insurers") include an insurance company (e.g., BlueCross® BlueShield®, Aetna® Inc., etc.), Health Maintenance Organization ("HMO"), Preferred Provider Organization ("PPO"), third-party administrator (TPA), Self Insured/Self Funded Employer, or local, state, or Federal Government (e.g., Medicare) and their approved intermediaries including private insurers providing Medicare or Medicaid health insurance in coordination with, or on behalf of, the Government (e.g., BlueCross® BlueShield® of South Carolina provides and administers Medicaid and Medicare insurance), as examples. The insurers generally negotiate with the service providers (e.g., hospitals, doctors, etc.) various terms, including the amounts (and corresponding conditions) that the insurers will pay the service providers for services rendered to the consuming members of the insurers. For instance, a negotiated contract may specify that an insurer will pay a service provider X amount for performance of a given healthcare service (e.g., caesarean-section procedure, open heart surgery, blood test, routine physical exam, LASIK eye surgery, dental root canal, prescribed pharmaceuticals, healthcare equipment (e.g., wheelchair), etc.) for one of its members. The contract may specify those healthcare services for which the insurer will reimburse the service provider, as well as the corresponding reimbursement rates for each service. That is, the contract may define how the reimbursement is to be computed for each service. For instance, the contract may list things that are not covered and/or may specify that certain items are limited in the number of services that are allowed.

Once the service is provided and the claim is submitted, then a claim processing and adjudication system may be used to evaluate the claim under the insurer's contract with the service provider, etc. and determine the insurer's liability as well as the consumer's liability for such service. In general claim adjudication refers to determination of liability of one or more parties (e.g., the patient/member, insurer, service provider, etc.) for a given healthcare service based on pre-defined relationships/responsibilities (e.g., the above-described contracts between the insurer and service provider and/or contracts between the member or member's employer, etc. and insurer). Such claim adjudication typically includes evaluation of the member's specific health benefit plan and status of their accumulators/financial accounts associated with their benefit plan to arrive at a determination of liability for the member/patient and/or insurer. Adjudication typically calculates patient liability based on such features as: 1) provider contracted rates/network benefit, 2) member's specific health benefit plan, 3) member's specific financial balances, accumulators, and accounts (deductibles, visits allowed/used, HRA, HSA, FSA, etc.), and 4) clinical edits for the member and their benefit plan. Traditional claim adjudication systems process received claims to adjudicate them (i.e., determine liability of the parties), and post/commit the adjudicated claim for payment by an insurer, in response to which funds are distributed from the insurer for the insurer's determined liability.

As described further herein, typically medical claims are adjudicated to determine the insurer's liability as well as the consumer's liability for medical services rendered by a medical service provider, such as a physician, hospital, etc. Similarly, in the event that pharmaceuticals (e.g., drugs, equipment, etc.) are prescribed, pharmaceutical claims are adjudicated to determine the insurer's liability as well as the consumer's liability for such pharmaceuticals rendered by a pharmaceutical service provider (or "pharmacy").

Today, more than half of patient visits to physicians result in prescriptions, and most serious medical conditions are treated with one or more prescription medications. Experts at the Institute of Medicine estimate that 30-40% of hospitalizations are directly or indirectly associated with improper use of prescription drugs. Some 213,000 hospital emergency visits in 2005 were attributed to use or misuse of prescription painkillers alone. With expanded prescription drug coverage in the federal Medicare Program (Part D), the potential for inappropriate, as well as appropriate, drug use increases exponentially. Finally, drug costs during the past decade have experienced the most rapid rise of any component of medical service expense.

A consensus of recent research shows that proper and timely use of prescription drugs can prevent or ameliorate acute flare-ups in chronic conditions that are both dangerous and costly. However, major American corporations are eliminating or cutting co-pays for drugs for their employees, such as those for treating heart conditions, asthma, and diabetes (see e.g., Wall Street Journal, May 8, 2007, Personal Journal page D1). As a consequence, insurers seek information not only on the cost of drugs but on how, by whom, and whether they are used.

Yet, currently available computer-implemented methods dealing with pharmacy claims provide limited information. For instance, no currently available computer-implemented methods dealing with pharmacy claims provide information (a) in a clinically relevant time frame using (b) drug- and diagnosis-neutral measures and (c) transparent interactions between patients, prescribing physicians, and prescription drugs that (d) preserve evidence of the prescribing physician's clinical intent and (e) the patient's compliance, and that allows for (but does not require) (f) correlation with relevant medical claims.

Certain historical dimensions of the health care insurance industry are relevant to the context of the concepts presented herein. The first is that pharmacy benefits coverage has not been an integrated component of "standard package" medical insurance. As a consequence, both data and payment systems for pharmacy have historically been separate from those systems for other medical services, such as hospitalization and all aspects of physician and other professional care. One consequence is that even as the standard medical insurance benefit has been extended to pharmacy coverage, both data management and payment systems have remained separate domains. Whereas most health care insurers receive, manage, pay, and analyze their own medical claims, pharmacy claims activities are sub-contracted to Pharmacy Benefit Management (PBM) companies. As discussed below, PBM responsibilities for pharmacy claims analysis tends to be of limited scope.

Existing methods for dealing with pharmaceutical claims are of three general types. The most common type is cost-oriented methods employed by the PBMs. The second type uses methods that subsume pharmacy records within episodes defined by medical claims (hospital, other inpatient, outpatient, or professional claims containing medical diagnosis codes). The third type uses methods that aggregate pharmacy records over some extended time period, using the specific drugs prescribed as proxies for medical condition diagnoses, in order to calculate a patient's relative risk of incurring future medical expense. Each of these three pharmaceutical claim use types are discussed further below.

The presence of pharmacy benefit managers (PBMs) in third party (e.g., health care insurer) claims adjudication systems for payment of pharmacy claims is well established in the industry. A typical PBM receives a claim that is generated when a patient has a prescription from a doctor filled at a pharmacy, and the PBM determines if the drug prescribed is part of the patient's insurance coverage. If the drug is within the patient's coverage, the claim is paid. In some PBM systems, the claim is further examined in attempt to detect fraud, to determine provider utilization of certain drugs, and to encourage the use of generics. However, in the analysis of the pharmacy claims for these additional uses, the PBM does not allow for correlation of the pharmacy claim to another pharmacy claim except as a duplicate, as a substitute generic drug, or for cost review. It also does not allow for correlation to a medical claim. PBM-produced cost tracking reports are typically aggregated to plan or aggregate provider (IPA, clinic) level, but are available within 30 days of pharmacy events.

The second most common type of pharmacy grouper subsumes pharmacy claim data into medical episode grouping logic based on diagnosis codes in medical claims, such as those generated by hospitals, other inpatient facilities, outpatient clinics, and professional providers for billing insurers. Pharmacy claims are treated as incidental to medical claims which are grouped by diagnosis code(s) or relationships between diagnosis and procedure code(s) according to dates of service and prescribing providers. When pharmacy claims cannot be associated with the medical claims based on dates of service and prescribing provider, they are simply listed as pharmacy events based on drug, date, and prescribing provider so as to be associated with the patient/member or provider as a component of total cost. The pharmacy claims are not analyzed for utilization patterns within drugs or relationships between drugs; they are not classified by type, identified as Multi-Drug or Concurrent, and they do not establish intervals for monitoring patient compliance; and they provide no mechanism to analyze medication coordination among multiple prescribing physicians. Examples of this method is Episode Treatment Groups (ETGs) offered by Ingenix, Inc., and the methods described in U.S. Pat. No. 5,918,208 titled "System for providing medical information," U.S. Pat. No. 5,557,514 titled "Method and system for generating statistically-based medical provider utilization profiles," U.S. Pat. No. 6,223,164 titled "Method and system for generating statistically-based medical provider utilization profiles," and U.S. Pat. No. 7,222,079 titled "Method and system for generating statistically-based medical provider utilization profiles." Because such ETGs systems operate on medical data typically spanning 12 to 36 months, the information produced has limited clinical relevance and currency; rather, it is used largely in pricing services, financial planning, and cost management applications.

The third type of pharmacy grouping method in current use does not attempt to construct either medical or pharmacy episodes, but rather groups evidence of medical diagnoses and drugs from all providers over a period of time to predict a patient's "risk"—that is, a health plan member's probability of consuming future resources, measured in dollars, either for total medical consumption or for prescription drugs alone. Future risk is predicted based on the most recent 6 to 24 months of pharmacy claims (or pharmacy and medical claims). Specific drug codes and therapeutic classes are classified and grouped as proxies for implied disease states, with each diagnostic condition assigned a weighting factor for probable future cost (risk). A patient's drug use is considered in aggregate, with no attention to temporal sequence, prescribing physician, dosage or supply, whether used in a multi-drug therapeutic strategy or concurrent with other drugs, continuity, or any other aspect of a physician's clinical intent or a patient's pattern of use and compliance. Examples of this method include DxCG's Diagnosis Cost Groups (DxCGs), Johns Hopkins University's Adjusted Clinical Groups (ACGs), and Pharmacy Risk Groups (PRGs), the latter also owned and distributed by Ingenix, Inc. (like the above-mentioned ETGs).

BRIEF SUMMARY OF THE INVENTION

In view of the above, a desire exists for improved utilization of pharmaceutical claims data. For instance, a desire exists for systems and methods for grouping, categorizing, and profiling pharmaceutical claims data within a clinically relevant time frame. Similarly, a desire exists for logically consistent non-disease based rules for episode boundaries (start and end dates) that are applicable regardless of medical condition, treatment setting, or drug type. Finally, a desire exists for systems and methods for associating drug treatment strategies with specific physician prescribers, making it possible to recognize whether drug treatment complexity results from single or multiple sources.

Embodiments of the present invention provide a computer-implemented method for grouping, categorizing, and profiling pharmaceutical claims data to assist health care managers in determining (a) medication treatment experience, outcomes, and medication compliance behaviors of patients and (b) appropriate drug prescribing, medication coordination, and cost-efficiency of health care providers. An objective means is provided for categorizing and quantifying patterns of prescription drug utilization as a health care service within a clinically relevant time frame. A pharmacy episode group (PEG) is a pharmacologically homogenous grouping of drugs with the same therapeutic ingredients used by a patient once or over an extended period of time. The PEG is a patient-centered pharmacy classification unit, which uses script-level pharmacy claim data as input data and assigns each script to the appropriate episode. Pharmacy episodes are categorized based on algorithms linking the pattern of a physician's recommended use (drug supply) and the patient's pattern of compliance (intervals between fill dates). The system also identifies multi-drug and concurrent use drug episodes, flags patients' records where intervals between scripts suggest non-compliance with recommended therapy, selects the most recent claims, resets windows (episode start and end dates), and ultimately assigns all pharmacy claims to episodes.

Accordingly, it is a broad aspect of the present invention to provide a computer-implemented system and method for grouping, categorizing, and profiling pharmaceutical claims data.

Certain embodiments of the present invention provide a system and method that offer an objective means for categorizing and quantifying patterns of prescription drug utilization as a health care service within a clinically relevant time frame. A pharmacy episode group (PEG), as used herein, generally refers to a pharmacologically homogeneous grouping of drugs with substantially the same therapeutic ingredients used by a patient once or over an extended period of time. According to certain embodiments, a PEG grouper method is provided that uses line-item pharmacy claim data as input data and assigns each pharmacy record to a patient and to the appropriate pharmacy episode.

Certain embodiments of the present invention provide a methodology for identifying, organizing, and grouping individual prescription pharmacy claims to construct pharmacy episodes for analysis of provider treatment patterns and medical management for health plan patients in general and for specific drugs and medical diagnoses. In certain embodiments, the PEG determines, for each pharmacy episode, a corresponding episode category. For instance, in one embodiment, the PEG determines for each pharmacy episode whether the subject pharmaceutical (e.g., drug) is being used as a "maintenance" therapy (e.g., taken on a regular basis, such as for controlling high blood pressure), as an "acute intervention" (such as an antibiotic for a bacterial infection like pneumonia), or as an "extended intervention" (e.g., for the patient to use as needed, such as for common gastrointestinal discomfort). The mutually exclusive algorithms for assigning episode category (e.g., ME for Maintenance Episode, AI for Acute Intervention episode, and EI for Extended Intervention episode) are inclusive of all pharmacy claims. Pharmacy episode categories may be based on a combination of a prescribing physician's use recommendations, recorded on the pharmacy claim as "supply" and evidence of a patient's utilization in the form of fill dates and intervals between fill dates in relation to drug supply.

In certain embodiments, the PEG is also used to determine whether each drug is being used in conjunction with another drug or drugs as a Multi-Drug (MD) treatment strategy, and whether any specific drug is being taken concurrently (CC) with another or several other drugs. Each drug is considered independently, the episode type is identified, and then its status as Multi-Drug and/or Concurrent is established.

Thus, according to certain embodiments, a computer-implemented pharmaceutical claims profiling system is provided that is operable to perform grouping, categorizing, and profiling based on pharmaceutical claims data. Thus, in certain embodiments such profiling system provides for pharmaceutical claims grouping, categorizing, and profiling. For example, in certain embodiments, the pharmaceutical claims are processed to be assigned to corresponding pharmaceutical episodes, and each episode is then categorized as either ME, AI, or EI. In addition, profiling may be performed for determining whether a given drug is being used as a MD treatment strategy. For example, in addition to creating the episode and classifying it by type, the PEG identifies each prescriber contributing to an episode, making it possible to distinguish whether inappropriate treatment patterns result from single or multiple sources.

According to certain embodiments, the computer-implemented pharmaceutical claims profiling system advantageously offers an objective means for categorizing and quantifying patterns of prescription drug utilization as a health care service within a clinically relevant time frame.

According to certain embodiments, the computer-implemented pharmaceutical claims profiling system utilizes line item pharmacy claim data as input data. The system is operable to process such line item pharmacy claim data to determine the pharmaceutical episodes, and to categorize the pharmaceutical episodes, as discussed further herein.

According to certain embodiments, the computer-implemented pharmaceutical claims profiling system assigns every pharmacy claim contained in received pharmacy claim data to a patient. According to certain embodiments, the computer-implemented pharmaceutical claims profiling system further assigns each pharmacy claim to a pharmacy episode. Additionally, in certain embodiments, the computer-implemented pharmaceutical claims profiling system identifies new or repeat pharmacy episodes.

Further, in certain embodiments, the computer-implemented pharmaceutical claims profiling system assigns each pharmacy episode to an appropriate pharmacy episode category, such as the categories of "maintenance" therapy episode, "acute intervention" episode, and "extended intervention" episode. In certain embodiments, the computer-implemented pharmaceutical claims profiling system includes such categorization of pharmacy episodes based upon algorithms relating to physician's use instructions and/or patient's patterns of compliance with physician-indicated use of the drug(s).

According to certain embodiments, the computer-implemented pharmaceutical claims profiling system identifies the patient's compliance with physician-indicated use of the drug(s).

According to certain embodiments, the computer-implemented pharmaceutical claims profiling system addresses every pharmacy claim received and assigns each received pharmacy claim to one of a plurality of different episode categories (e.g., "maintenance" therapy, "acute intervention", and "extended intervention") with specific "start" and "end" dates based on rules for "intervals" between physician's instructions for days of treatment (supply) and patient's prescription fill dates.

Further, in certain embodiments, the computer-implemented pharmaceutical claims profiling system addresses every pharmacy episode and identifies those pharmacy episodes that are a component of a multi-drug episode. Further, in certain embodiments, the computer-implemented pharmaceutical claims profiling system addresses every pharmacy episode and identifies those pharmacy episodes that are concurrent with one or more other pharmacy episodes.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

As used herein, "pharmacy records" generally refer to claims that represent a prescription filled for a patient, typically at a retail pharmacy, the first instance of which is usually initiated by a service rendered by a physician or physician-authorized provider engaging in the direct evaluation, management, or treatment of a patient. Such pharmacy claims are typically submitted (e.g., electronically) to a claim adjudication system, such as that of a PBM, which adjudicates the claim data to determine financial responsibility of the consumer (patient) and a third-party payer (e.g., insurer). Refills of the same drug/script may be authorized within the initiating prescription or, more recently, they may be initiated by a patient's communication with a physician via telephone or e-mail.

According to one embodiment, grouping prescription drug records to episodes involves two interacting tables. The first table is a National Drug Code (NDC) table, which has in excess of 200,000 entries. Every pharmacy record contains one unique National Drug Code (NDC). The National Drug Code is a standard 11-digit identifier for each drug product, as recognized by the Centers for Medicare and Medicaid (CMS), other federal and state agencies, and most commercial enterprises. It is unique to each specific pharmaceutical product. The first 5 numbers identify the manufacturer of a product. The second 4 numbers identify the product (chemical composition/ingredients), and the last 2 numbers identify the package size of that product.

The second table is a smaller drug identification table. Certain embodiments of the present invention employ the smaller drug identification table to map NDC codes to a unique drug identification number ("drug_id"), a clinically unique identifier for the chemical(s) that constitutes a drug's pharmaceutical ingredient(s). According to certain embodiments, the computer-implemented pharmaceutical claims profiling system constructs pharmacy episodes based on the unique drug identifier (drug_id) so that differences between brand names or generic product names or packaging modes indicated by different NDC codes do not interrupt episode formation and continuity. At the same time, in certain embodiments, the computer-implemented pharmaceutical claims profiling system retains the NDC code submitted on the record both for verification and for users of the profiling system to perform secondary analysis, such as analysis regarding use of generics versus brand drugs.

Figure 1:
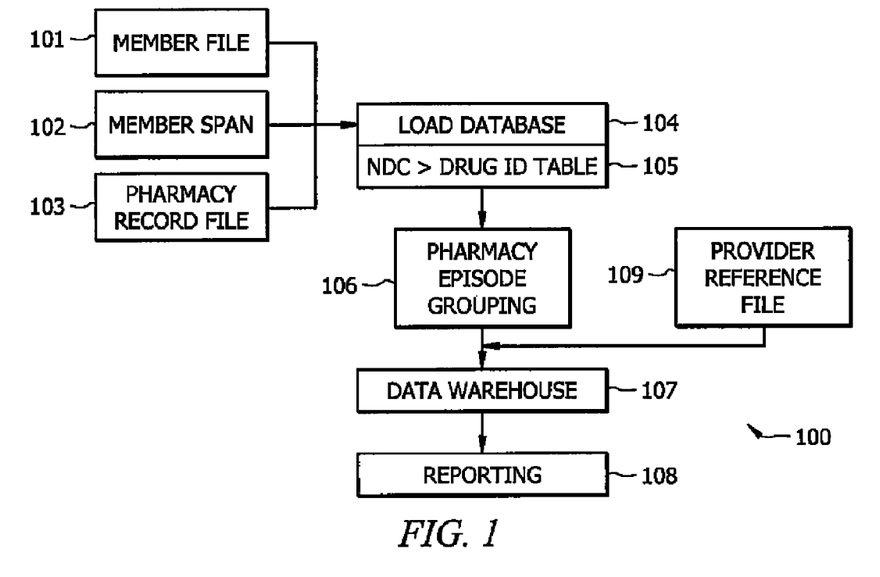
FIG. 1 shows a block diagram of a system according to one embodiment of the present invention.

FIG. 1 shows a block diagram of a system 100 according to one embodiment of the present invention. In this example, a Member file 101 contains a member's unique identifying number (Medicare or insurance plan ID). In addition, such member file 101 may further contain demographic information such as age, sex, and other data elements that might be used in secondary analysis. Such data may be stored digitally as computer-readable data stored to a computer-readable medium (e.g., hard disk, memory, magnetic storage device, optical storage device, etc.). The data may be stored in any readable format, such as a flat file, table, database, or other type of data structure.

A Member SPAN file 102 contains, for each unique member identification number, information on dates of plan and pharmacy benefit eligibility (e.g., arranged by month). The computer-implemented pharmaceutical claims profiling system uses Member SPAN file 102 to validate that the member was enrolled and eligible for the pharmacy benefit on the date that a pharmacy record indicating that a prescription has been filled is generated. Such data of Member SPAN file 102 may be stored digitally as computer-readable data stored to a computer-readable medium (e.g., hard disk, memory, magnetic storage device, optical storage device, etc.). The data may be stored in any readable format, such as a flat file, table, database, or other type of data structure.

A Pharmacy Record file 103 contains the member's unique identifying number, the NDC code identifying the drug prescribed, the provider identifying number for the prescriber, the date when the prescription is filled by a retail or other (such as clinic) pharmacy, and the number of days of treatment supplied. While such pharmacy records included in Pharmacy Record file 103 may contain other data elements that may be of interest for subsequent analysis, preferably at least the following five fields are included for each record: member ID, NDC, prescribing provider ID, date filled, and days (of treatment) supplied. The data of Pharmacy Record file 103 may be stored digitally as computer-readable data stored to a computer-readable medium (e.g., hard disk, memory, magnetic storage device, optical storage device, etc.). The data may be stored in any readable format, such as a flat file, table, database, or other type of data structure.

According to certain embodiments, the computer-implemented pharmaceutical claims profiling system is implemented to confer "production-scale" operation capable of handling hundreds of thousands of pharmacy claims simultaneously.

Pharmacy claim data is input electronically as data records into a computer storage device, such as a hard disk drive. The inventive pharmacy claims profiling system may reside in any of a number of computer system architectures. For instance, such computer-implemented pharmaceutical claims profiling system may be run from a stand-alone computer or exist in a client-server system, for example a local area network (LAN) or wide area network (WAN).

Once relevant pharmacy claim data is input, the pharmacy claims data is processed by the system by loading a computer-executable program into the computer system memory. During set-up of the program onto the computer system, the computer program will have previously-set pointers to the physical location of the data files and look-up tables written to the computer storage device.

According to one embodiment, the ETL (Extract Transfer Load) process of the pharmacy claims profiling system is controlled by a file containing XML code with a node per load module that is executed as in the following exemplary code:

The minimum input files employed for one exemplary implementation of the pharmaceutical claims profiling system are as follows, and are described in greater detail above:
1. Member file 101 (containing unique member identifying number and, in some cases, demographic data);
2. Member Span file 102 (containing dates of eligibility by month and other data);
3. Pharmacy Claims (or Record) file 103 (containing prescribing provider ID, NDC, fill date, days supply); and
4. NDC table to DrugID Table 105, Crosswalk (updates periodically, e.g., twice a year)

The operations performed for loading pharmacy claim data to be processed by this exemplary embodiment of system 100 include the following:

Step 1. The PDM Loader process 104 reads in the raw data files 101-103, scrubs the data, and validates the input. It is then ready for pre-aggregation as input into the pharmaceutical claims profiling logic. In one embodiment, input data is split into smaller member-based files to allow more efficient processing and also allow for distributed processing, if so desired.

```
-----------------------------------------XML CODE START---------------------------------
<Loader>
<LoadModule Name="tbDimTime" Seq="A" Type="">
<Success Status="1" FileCreated="0" Cleaned="0" Detail="0" LastCount="0" /></LoadModule>
<LoadModule Name="MemberType" Seq="B" Type=""><Success Status="1" FileCreated="0"
Cleaned="0" Detail="0" LastCount="0" /></LoadModule>
<LoadModule Name="SpanType" Seq="C" Type=""><Success Status="1" FileCreated="0"
Cleaned="1" Detail="0" LastCount="0" /></LoadModule>
<LoadModule Name="PharmacyType" Seq="F" Type=""><Success Status="1" FileCreated="1"
Cleaned="1" Detail="0" LastCount="0" /></LoadModule>
<LoadModule Name="PostLoadProcess" Seq="H" Type=""><Success Status="1" FileCreated="0"
Cleaned="0" Detail="0" LastCount="0" /></LoadModule>
</Loader>
----------------------XML CODE END-----------------------------------------------------
```

Input files are copied to an input location which is configurable in the application configuration file. The application configuration is updated to indicate the number of input files for each load module. The input files are then renamed to be the same as the corresponding filename key, e.g. if there are two Pharmacy files, rename Pharmacy1, Pharmacy2 and set number of files for Pharmacy to 2.

This process can be automated by enhancing the integration engine to support job sequencing and creating a job to listen to a folder. The interface to a user may then be a Web application (browser), for example.

Data on which the pharmaceutical claims profiling system operates, according to this embodiment is received and input in the form of flat files (or other appropriate form, such as tabular form, database, etc.) received from clients in conformity with a Data Specification document provided to the client. Client data undergoes a three step process, in this exemplary embodiment, to end up in a relational data warehouse 107.

The application that reads and processes the flat file data is called the PDM "Loader", and it performs the load database operation 104 shown in FIG. 1. Preferably, the PDM Loader is part of the PDM Integration Engine family of classes and can be configured to run as an Integration Engine job. According to one embodiment, the PDM Loader design also allows for a distributed processing architecture by means of splitting large input data into much smaller files, so-called "atomic" input data.

Step 2. The PDM Loader process 104 loads some tables 105 into the Load database and some tables directly into the data warehouse 107.

Step 3. A Post-Load process checks for duplicates and identifies data updates (new inputs) that might close or extend an episode.

In one embodiment, the Load process 104 is largely file-based, rather than database-reliant to support scalability for larger amounts of input data. This exemplary design also lessens reliance on a single-threaded, single-resource (SQL Server database) and allows for a multi-resource, multi-threaded load system, if so desired.

According to one embodiment, the basic PDM Loader class can be initiated from the PDM Integration Engine (which is a Windows Service). Splitting large input files into smaller atomic files may leverage the fact that a member is the basic atomic unit within the load process. In fact, it is possible for the PDM Load application to run in entirety on a single member. This non-reliance on member interaction permits splitting input data based on groups of members. In one embodiment, the PDM Loader application assigns members to groups simply by dividing the total member count by a configurable value (e.g., 100 to then get 100 smaller member groups). Each member group is then sent through load processing modules. Each module represents unique load logic, so for example there may be a load module for Pharmacy Claims.

Irrespective of how the pharmacy claims data may be loaded, such data may then be processed to form corresponding pharmacy episode groupings, which may in turn be categorized (or classified) into corresponding categories. The process of grouping the received pharmacy records (pharmacy claim file) into pharmacy episodes, according to one exemplary embodiment, utilizes a minimum of six contiguous months of pharmacy claims, which can be added to continuously at monthly or quarterly intervals. Each update will address the previous as well as new incoming pharmacy records and either reclassify "open" episodes based on new information or "close" them.

In general, a pharmacy episode "start date" is set at the first instance of specific drug (drug_id) in each patient's pharmacy claims. A pharmacy episode "end date" is set at the latest prescription fill date for that drug_id in the pharmacy claims plus the physician's indicated "days supply" for treatment.

Episode creation, according to one embodiment, performs a series of passes through the claim load, which is sorted by Member_ID by prescription fill date (date of service), to apply the rules that distinguish the three types of episodes—Acute, Extended, and Maintenance—and to identify episodes that represent a Multi-Drug therapeutic strategy and also to identify drugs that are being used concurrently with other drugs.

The first pass through the pharmacy records creates a new field which is added to each pharmacy record to enable episode identification and classification. For each Member ID, at the first instance of a Drug_ID, label 001-01, which represents episode 001, script 1. If the same Drug_ID occurs for that Member ID, label the record 001-02, which represents episode 001, script 2.

At the first instance of a different Drug_ID, label the record 002-01, representing episode 2 and script 1. Increment each successive new DrugID for that member, labeling records as 003-01, 003-02, 003-03, through to the end of each member's records in the claim load.

The second pass is to establish episode boundary dates and classify episodes by type into either a Maintenance Episode, Acute Intervention, or Extended Intervention, as discussed below.

A) Maintenance Episode. If an identical Drug_ID recurs three or more times, and the intervals between successive fill dates are less than two times the days supply, label as "maintenance episode." (Depending on the analytic period (claim load), the first instance of any Drug ID could be marked either as "new" or "refill," so this information, if present, is ignored.)

Example: Drug ID 001-01 fill date is Mar. 10, 2006 and days supply=30. If 001-02 takes place before May 10, 2006, and 001-03 takes place in fewer than 60 days after 001-02, this is a "Maintenance Episode" (ME-01) but if 001-02 or 001-03 takes place more than 60 days later than the preceding fill date, this will be an EI (Extended Intervention) episode.

The Maintenance Episodes Boundary is established by first fill date and last fill date plus days supply converted to "begin" and "end" dates, respectively (mm/dd/yyyy). (The boundary may be equivalent to the analysis period if supply is continuous.) In the example above, episode begin date is Mar. 10, 2006 and the end date is the last fill date plus the days supply. If the analysis period were Jan. 01, 2006 to Dec. 30, 2006 and the last fill date was Dec. 10, 2006, the "end date" would be Jan. 09, 2007.

To designate Episode Type and Episode Type Number a new five-digit field is created and added to each pharmacy record. Possible field values are: ME-01 through ME-99 Maintenance Episode. To designate Episode Begin/End Dates, a new 17-digit field is created and added to each record, as follows: MMDDYYYY-MMDDYYYY B) Acute Intervention. Identify member with a unique DRUG-ID script (or scripts) and no more than one refill at an interval less than two times the first script's days supply. If the date for the next script with the same Drug ID is greater than two times the first scripts days supply, begin EI (Extended Intervention) episode.

Example: New Drug ID episode 003-01 fill date Jul. 7, 2006 with days supply=15. If 003-02 occurs before Aug. 7, 2006 (double the days supply), then label as a Acute Intervention episode (AI-01). If fill-date occurs on Aug. 8, 2006 or after, label as Extended Intervention episode (EI-0?).

The Acute Intervention Boundary is established by first fill date and last fill date plus days supply, converted to start/end dates: mm/dd/yyyy-mm/dd/yyyy.

The designation of Episode Type and Episode Type Number is achieved by creating a new five-digit field. Possible field values are: AI-01 through AI-99 Acute Intervention Episode. Episode Begin/End Dates are recorded in a new 17-digit field appended to the pharmacy record.

C) Extended Intervention. Identify member with "new" Drug ID script where the interval between the original fill date and subsequent "refill" claims is three times or more than the days supply for the original script For example, new Drug ID script 004-01 fill date is Apr. 12, 2006 and days supply is 10. If refill date occurs before May 02, 2006, then it is AI. If the next fill date is May 03, 2006 or later, it is EI.

The EI Boundary is established by first "fill date" and last fill date plus days supply. If the next script same Drug ID date is more than six times the days supply of the last fill date, begin new episode.

The designation of Episode Type and Episode Type Number are achieved by creating a new five-digit field. Possible field values are: EI-01 through EI-99 Extended Intervention Episode. Episode Begin/End Dates are indicated by a new 17-digit field appended to each record, MMDDYYYY-MMDDYYYY.

The third pass identifies episodes as Multi-Drug episodes and identifies episodes of one drug that are concurrent or overlapping with use of other drugs. To identify Multi-Drug episodes and Concurrent episodes, distinct two-character fields are created: MD for Multi-Drug and CC for Concurrent. During processing in this third pass, the system identifies all episodes where two or more Drug IDs have SAME "fill date" and SAME "provider," and those identified episodes are marked as "Multi-Drug"—MD. Also, during this third pass, the system labels any episode type as "CC" where the "fill date" plus "days supply" is overlapping any other date interval with the same Member ID and different Drug ID.

Operationally, one may designate a date when episode groupings will need to reset and be calculated from the start point again. In this case, episode sequence numbers will restart based on a date in the system or calculation of specified days.

Figure 2:
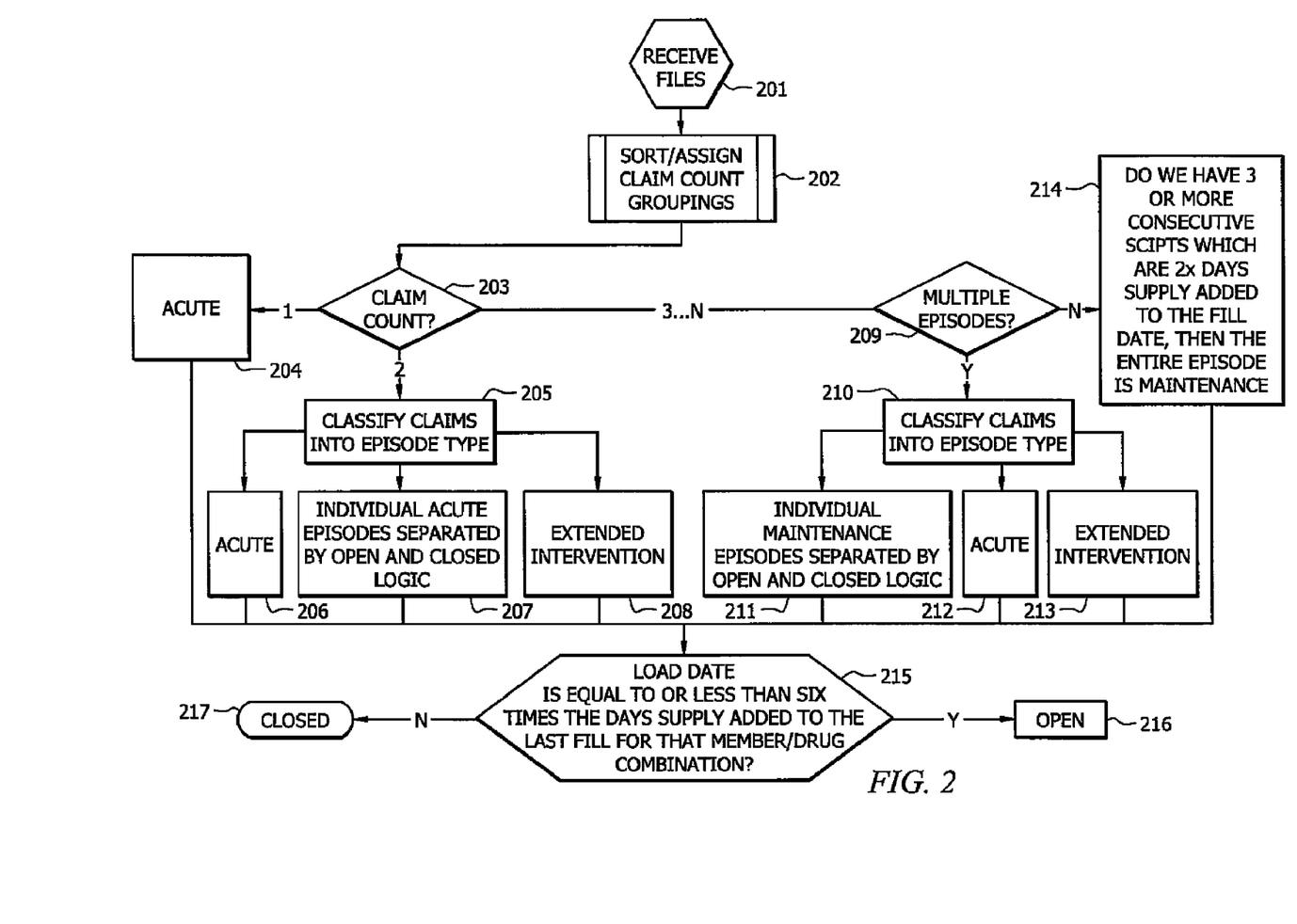
FIG. 2 shows an exemplary flow of logic in generating pharmacy episode groupings from the received pharmacy claims, member, span and provider files according to one embodiment of the present invention.

FIG. 2 shows an exemplary flow of logic in generating pharmacy episode groupings from the received pharmacy claims, member, span and provider files according to one embodiment of the present invention. This process flow identifies when it is necessary to flag an episode as open (in block 216) or closed (in block 217) based on the operations described below.

Block 201 represents the entry point or receipt of these four data files in the system. The received claims are classified and sorted into three distinct groups in operational block 202. According to one embodiment, each group is separated from the minimum date and maximum date of the current pharmacy record claims file in the data load. The first group is the single claim instance. The next is the two-claim instance and the last group is the three or more claim instances. Thus, in operational block 203, the claims of the first group (single claim instance) are directed to block 204 for processing, the claims of the second group (two claim instances) are directed to block 205 for processing, and the claims of the third group (three or more claim instances) are directed to block 209 for processing. Each claim group thus represents a path for the PEG system logic to build episodes where each set of claims meets the criteria for Acute, Maintenance and Extended Intervention.

In this exemplary embodiment, the system defines an Acute Episode as a member with a "new" drug_ID script (or scripts) and no more than one refill at an interval less than two times the first script's day's supply. A Maintenance Episode is where an identical Drug_ID recurs three or more times, and the intervals between successive fill dates are less than two times the days supply. An Extended Intervention is defined as a "new" Drug_ID script (or Scripts) and subsequent "refill" claim or claims where the interval between the original and subsequent refill "fill date" is three times or more than the days supply for the original script.

In the first sort group, the single claim, a single pharmacy record is classified in block 204 as an Acute Episode if it meets the criterion: no more than one refill at an interval less than two times the first script's days supply. Operation then advances to block 215 where the process checks whether the episode can be considered Open (block 216) or Closed (block 217), as discussed further below.

In this embodiment, the system defines an episode as Open if the Load Date is equal to or less than six times the days supply added to the last fill date for that member/drug combination. An episode is Closed when the Load Date is greater than six times the days supply added to the last fill for that member/drug combination.

In the second sort group, where there are two pharmacy records in a given data load for a given member/drug combination, there are three possibilities for classification of the claim in block 205. (1) If two claims meet the criteria for classification as an Acute Episode, and fall within six times the days supply added to the last fill for that member/drug combination, then the system classifies them into one acute episode in block 206. (2) If the system determines that one claim falls within six times the days supply added to the last fill date for that member/drug combination and one is greater than six times the days supply added to the last fill for that member/drug combination, then it determines that there are two separate Acute episodes in block 207. (3) If the interval between the original and subsequent refill "fill date" is three times or more than the days supply for the original script, the system classifies this episode as an Extended Intervention in block 208. The operation then advances to block 215 where the process checks if the episode can be considered as Open (block 216) or Closed (block 217).

In the third sort group, which has three or more pharmacy records (3 . . . N) with the same member ID/Drug ID combination, the PEG system determines in block 209 whether the claims are all part of one episode or multiple episodes. If the intervals between successive fill dates are less than two times the days supply, all the records are classified as one Maintenance Episode in block 214. If the remaining claims for a given member/drug_ID combination meet other criterion, the system classifies them accordingly either as Acute in block 212, Individual Maintenance Episodes in block 211, or Extended Interventions in block 213. The operation then advances to block 215 where the process checks if the episode can be considered as Open (block 216) or Closed (block 217).

According to certain embodiments, new member, span, provider, and pharmacy records may be added monthly, quarterly, or at other frequencies to update existing episodes and to be processed for creation of new episodes. Episodes from the immediately preceding analysis periods may be revisited based on the latest data load (typically three months (one quarter)). As the system incorporates new data, the open/closed status, as well as classification (acute, maintenance, extended intervention, etc.) and concurrent status for all existing episodes, are re-evaluated.

Figure 3:
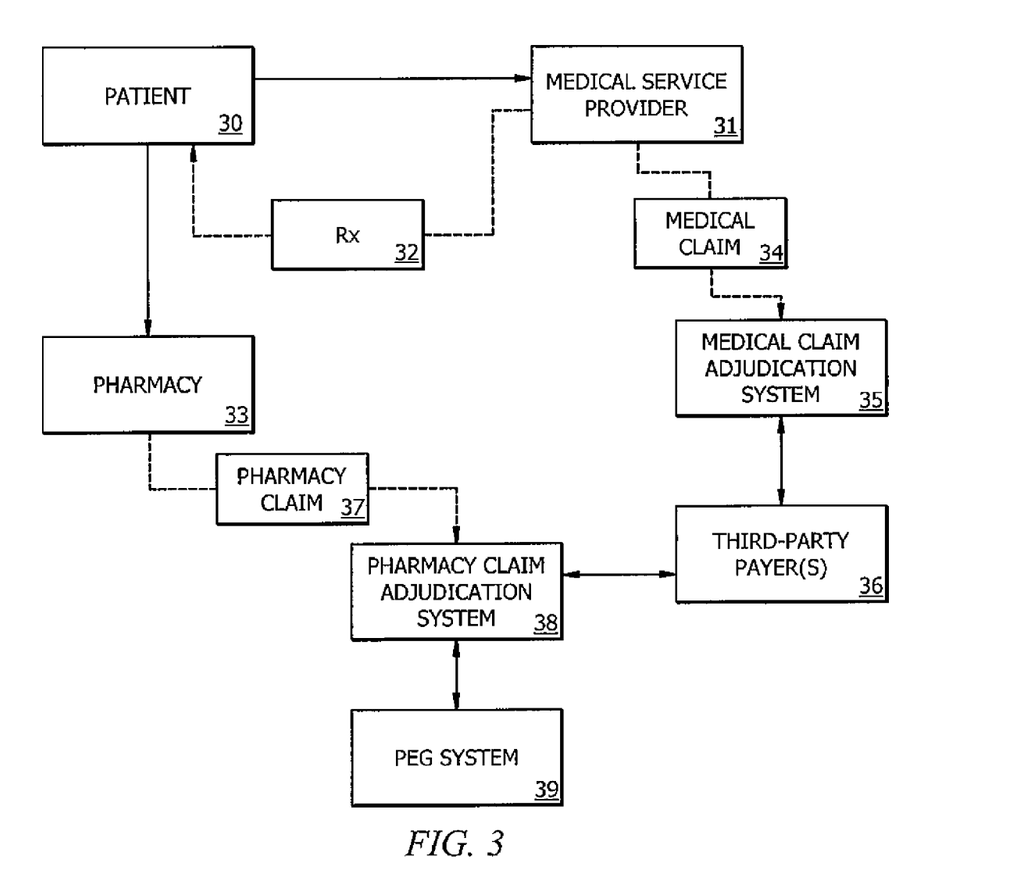
FIG. 3 shows a block diagram of an exemplary system in which an embodiment of the present invention may be implemented.

FIG. 3 shows a block diagram of an exemplary system in which an embodiment of the present invention may be implemented. Typically, a patient 30 goes to a medical service provider 31, such as a doctor, for treatment of a medical ailment. The doctor 31 examines the patient 30 and makes a diagnosis, and possibly gives the patient a prescription 32 for medication to treat the ailment. The patient 30 then leaves the doctor's office 31 and proceeds to fill the prescription 32 at a pharmacy 33.

The medical service provider 31 may submit (e.g., electronically) a medical claim 34 to a medical claim adjudication system 35 for the services rendered to the patient 30. The medical claim adjudication system 35 processes the medical claim to determine the financial responsibility of any third-party payer 36 (e.g., insurer) and that of the patient 30.

Similarly, when the prescription 32 is filled by pharmacy 33, a pharmacy claim 37 may be submitted (e.g., electronically) by pharmacy 33 to a pharmaceutical claim adjudication system 38, which may be a PBM for instance. The pharmaceutical claim adjudication system 38 processes the pharmacy claim 37 to determine the financial responsibility of any third-party payer 36 (e.g., insurer) and that of the patient 30.

Due to the complexities in submitting and processing many medical claims (e.g. accessing the correct form, correctly characterizing the visit, identifying the treatment accordingly, etc.), medical claims 34 for a given visit to a medical service provider may, in some instances, not be submitted for 90 days or more after the service is rendered. In contrast, pharmacy claims 37 are often submitted within a week of the prescription 32 being filled.

As shown in FIG. 3, in certain embodiments, PEG system 39 may be implemented to process the pharmacy claim data received by pharmacy claim adjudication system 38. Thus, for instance, in addition to adjudicating the received claims to determine financial responsibility of parties, the claim data may be further stored for processing by PEG system 39, e.g., according to the exemplary operational flow described above with FIG. 2.

An illustrative example of data fields that may be included in a pharmacy claim 37 is illustrated in Table 1 below:

TABLE 1

Figure 4:
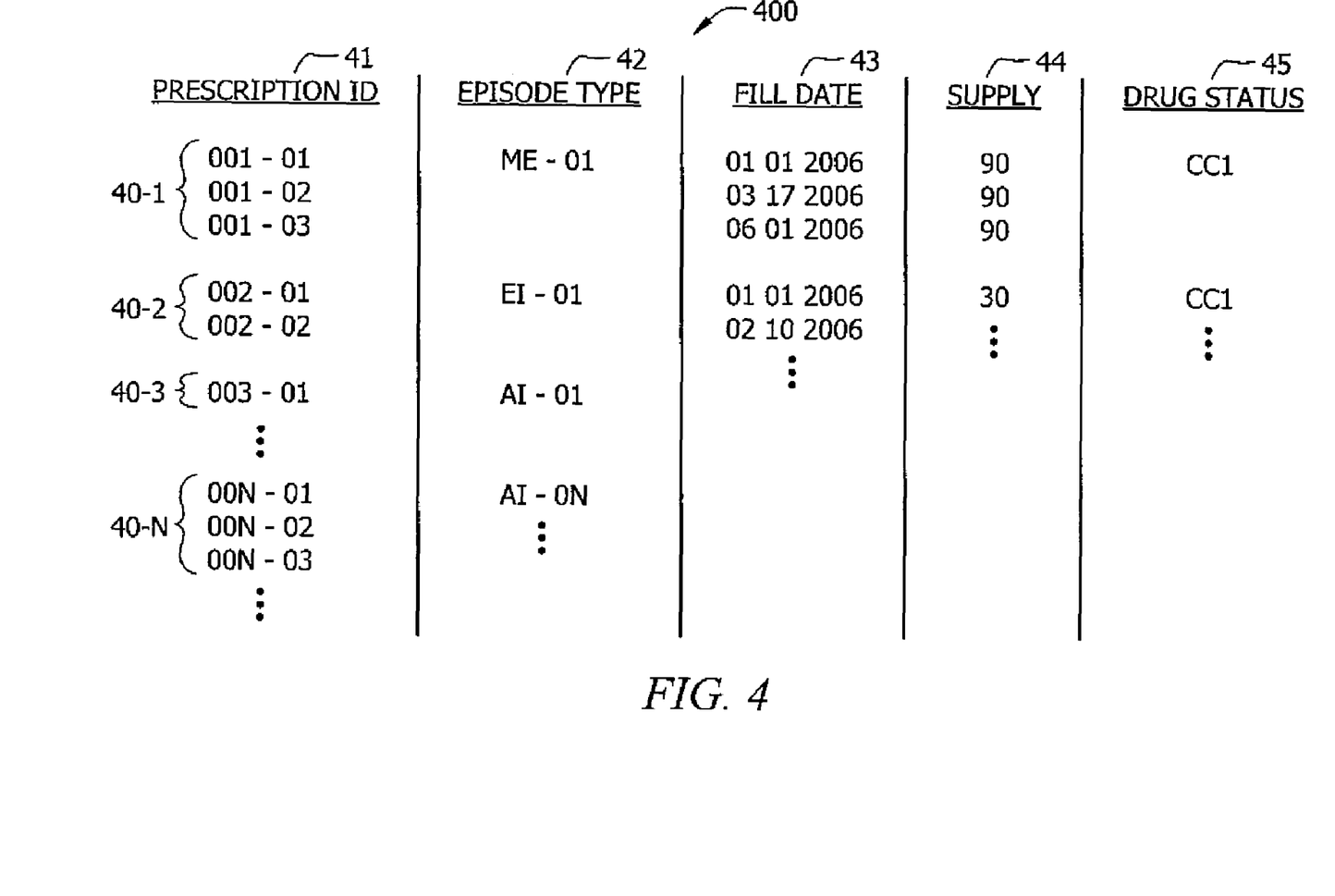
FIG. 4 shows an exemplary table illustrating groupings of episodes and claims according to one embodiment.

PlanID
HIC OR Member Number
Ordering Physician Provider ID OR
Ordering Physician DEA Number
Pharmacy ID
Prescription Number
New or Refill
NDC
Date Paid
Date Filled
Tier
Amount Paid
Ingredient Cost
Dispensing Fee
Copay Amount
Deduct Amt TABLE 1-continued Disallow Amt
AWP
Quantity
Days Supply FIG. 4 illustrates an exemplary data table 400 that may be employed/generated by the PEG system according to certain embodiments of the present invention. Each patient 30 for which pharmacy claims are submitted may have a unique data table 400 populated by PEG system 39 based on the received pharmacy claim data. A unique ID 41 is assigned for each prescription/drug contained in the received pharmacy claim data. In one embodiment, unique ID 41 is a six digit number assigned for the prescription. The prescriptions are grouped into pharmacy episodes in the manner discussed above, thus forming pharmacy episodes 40-1, 40-2, 40-3, . . . 40-N in the example of FIG. 4. Each of the pharmacy episodes is assigned a corresponding episode type (or category), which is stored in episode type column 42. As discussed above, the PEG system 39 may evaluate the pharmacy claim data for each determined episode to determine a corresponding type, such as ME (Maintenance Episode), AI (Acute Intervention episode), and EI (Extended Intervention episode).

Additional information may be stored in the table 400, which may be used for identifying pharmacy episodes, categorizing the episodes, and/or otherwise evaluating the episodes. Such information may include fill date 43 for each prescription/drug, the amount of supply 44 (e.g., 30 day, 90 day, etc.) for each prescription/drug, and/or a corresponding drug status 45 that may be determined by PEG system 39, such as an identification of whether each prescription/drug is being used in conjunction with another drug or drugs as a Multi-Drug (MD) treatment strategy or whether any specific drug is being taken concurrently (CC) with another or several other drugs.

When implemented via computer-executable instructions, various elements of embodiments of the present invention are in essence the software code defining the operations of such various elements. The executable instructions or software code may be obtained from a computer-readable medium (e.g., a hard drive media, optical media, EPROM, EEPROM, tape media, cartridge media, flash memory, ROM, memory stick, and/or the like).

Figure 5:
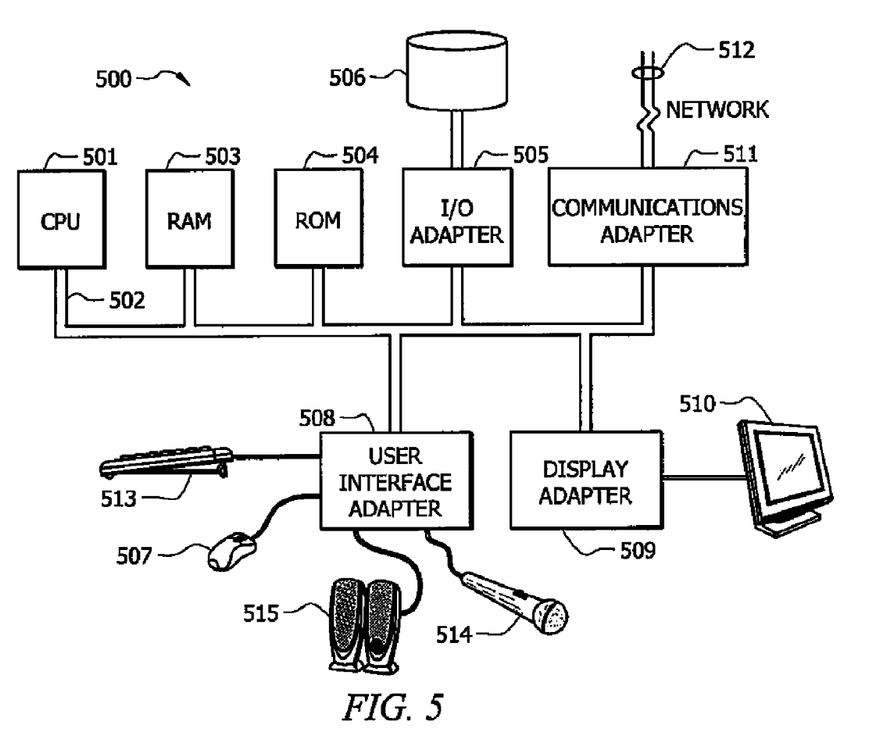
FIG. 5 shows an exemplary system on which embodiments of the present invention may be implemented.

FIG. 5 illustrates an exemplary computer system 500 on which software code implementing PEG system 39 may be implemented according to one embodiment of the present invention. Central processing unit (CPU) 501 is coupled to system bus 502. CPU 501 may be any general-purpose CPU. The present invention is not restricted by the architecture of CPU 501 (or other components of exemplary system 500) as long as CPU 501 (and other components of system 500) supports the inventive operations as described herein. CPU 501 may execute the various logical instructions according to embodiments of the present invention. For example, CPU 501 may execute machine-level instructions according to the exemplary operational flow described above in conjunction with FIG. 2.

Computer system 500 also preferably includes random access memory (RAM) 503, which may be SRAM, DRAM, SDRAM, or the like. Computer system 500 preferably includes read-only memory (ROM) 504 which may be PROM, EPROM, EEPROM, or the like. RAM 503 and ROM 504 hold user and system data and programs, as is well known in the art.

Computer system 500 also preferably includes input/output (I/O) adapter 505, communications adapter 511, user interface adapter 508, and display adapter 509. I/O adapter 505, user interface adapter 508, and/or communications adapter 511 may, in certain embodiments, enable a user to interact with computer system 500 in order to input information.

I/O adapter 505 preferably connects to storage device(s) 506, such as one or more of hard drive, compact disc (CD) drive, floppy disk drive, tape drive, etc. to computer system 500. The storage devices may be utilized when RAM 503 is insufficient for the memory requirements associated with storing data for operations of the PEG system 39. Communications adapter 511 is preferably adapted to couple computer system 500 to network 512, which may enable information to be input to and/or output from system 500 via such network 512 (e.g., the Internet or other wide-area network, a local-area network, a public or private switched telephony network, a wireless network, any combination of the foregoing). User interface adapter 508 couples user input devices, such as keyboard 513, pointing device 507, and microphone 514 and/or output devices, such as speaker(s) 515 to computer system 500. Display adapter 509 is driven by CPU 501 to control the display on display device 510 to, for example, display information pertaining to pharmacy claim data and/or pharmacy episode data, according to certain embodiments of the present invention.

It shall be appreciated that the present invention is not limited to the architecture of system 500. For example, any suitable processor-based device may be utilized for implementing PEG system 39, including without limitation personal computers, laptop computers, computer workstations, and multi-processor servers. Moreover, embodiments of the present invention may be implemented on application specific integrated circuits (ASICs) or very large scale integrated (VLSI) circuits. In fact, persons of ordinary skill in the art may utilize any number of suitable structures capable of executing logical operations according to the embodiments of the present invention.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:
1. A computer-implemented method comprising:
receiving, into a pharmacy episode grouping (PEG) system installed on a computer and being executed by a processor, pharmacy claims data records;
validating, by the PEG system, each of the pharmaceutical claims data records for a valid national drug code or a generic drug code to identify at least one drug, prescription use data for the at least one drug and a valid patient unique identifying number;

establishing, by the PEG system, for each unique patient identified, the number of validated pharmaceutical claims data records received for each drug identified;

grouping, by the PEG system, the validated pharmacy claims data records for each unique patient identified and each drug identified to one or more pharmacy episodes based upon a predefined algorithm;

sorting, by the PEG system, each pharmacy episode into one of at least three different groups, wherein the at least three different groups comprise a first group for episodes containing a single validated pharmacy claims data record, a second group for episodes containing two validated pharmacy claims data records, and a third group for episodes containing three or more validated pharmacy claims data records;

categorizing, by the PEG system, each pharmacy episode based at least one of on an interval length between pharmacy events stored in the validated pharmacy claims data records and the prescription use data for the at least one drug; and storing in a memory of the computer the validated pharmacy claims data records and their associated pharmacy episodes for monitoring usage of a prescription drug identified in the validated pharmacy claims data records.

2. The method of claim 1 further comprising:
applying the one predefined algorithm comprising a listing of constraints that defines each eligible pharmacy episode categorization for all pharmaceutical drugs based upon thresholds for the relationships between the supply of the drug and intervals between pharmacy events.

3. The method of claim 2 further comprising:
evaluating each validated pharmacy claims data record received into a pharmacy episode grouping (PEG) system to any open pharmacy episodes by category for each patient, and
grouping the pharmacy claims data record to the open pharmacy episode based upon the category constraints.

4. The method of claim 3 further comprising:
distinguishing intervals of patient non-compliance within the pharmacy episode category based upon data from pharmacy claims data records which do not conform to predefined algorithms setting thresholds for the relationship between the supply of the drug and intervals between pharmacy events.

5. The method of claim 1 further comprising:
differentiating pharmacy episodes based upon a predefined algorithm and data establishing multi-drug status.

6. The method of claim 1 further comprising:
differentiating pharmacy episodes based upon a predefined algorithm and data establishing its concurrent use status.

7. A computer-implemented method comprising:
receiving, into a pharmacy episode grouping (PEG) system installed on a computer and being executed by a processor, pharmacy claims data records and prescription use data for each prescribed drug identified in the pharmacy claims data records;

determining, by the PEG system, from the received pharmacy claims data records one or more corresponding pharmacy episodes;

sorting each pharmacy episode into one of at least three different groups, wherein the at least three different groups comprise a first group for pharmacy episodes containing a single pharmacy claims data record, a second group for pharmacy episodes containing two pharmacy claims data records, and a third group for pharmacy episodes containing three or more pharmacy claims data records;

categorizing, by the PEG system, the one or more corresponding pharmacy episodes into one of a plurality of different categories, wherein said categorizing comprises:
categorizing the one or more corresponding pharmacy episodes in the first group as an acute intervention (AI) episode when said single pharmacy claims data record for a given patient and prescription use data for a prescribed drug indicates a newly identified prescription and no more than one refill at an interval less than two times the prescription's days supply,
categorizing the one or more corresponding pharmacy episodes in the second group as a single acute intervention (AI) episode when said two pharmacy claims data records for the given patient and a prescribed drug each indicate no more than one refill at an interval less than two times the prescription's days supply, and fall within six times the days supply added to a last fill date of a most recently identified prescription;
categorizing the one or more corresponding pharmacy episodes in the second group as an extended intervention (EI) episode when said two pharmacy claims data records for the given patient includes a newly prescribed drug and subsequent refill claim or claims where the interval between the original and subsequent refill fill date is three times or more than the days supply for the original prescription of the drug;
categorizing the one or more corresponding pharmacy episodes in the third group as a maintenance episode (ME) when said three or more pharmacy claims data records for the given patient and a prescribed drug indicate the intervals between successive fill dates are less than two times the days supply; and storing the one or more pharmacy episodes and the respective category in a data table for monitoring usage of a prescription drug identified in the pharmacy claims data records.

8. The method of claim 7 further comprising:
determining whether each episode is an open or closed episode, wherein an episode is determined as open if a load date is equal to or less than six times the days supply added to the last fill date for that prescribed drug, and an episode is closed when the load date is greater than six times the days supply added to the last fill for that prescribed drug.

9. A computer-implemented method comprising:
receiving, into a pharmacy episode grouping (PEG) system installed on a computer and being executed by a processor, pharmacy claims data records and prescription use data for each prescribed drug identified in the pharmacy claims data records;

determining, by the PEG system, from the received pharmacy claim data records one or more corresponding pharmacy episodes; and categorizing, by the PEG system, the one or more corresponding pharmacy episodes into one of a plurality of different categories, wherein said categorizing comprises:
a) sorting each episode into one of at least three different groups, wherein the at least three different groups comprise a first group for episodes containing a single pharmacy claim record, a second group for episodes containing two pharmacy claim records, and a third group for episodes containing three or more pharmacy claim records;

b) categorizing episodes with a single pharmacy claim record into a first group as an acute intervention (AI) episode based on prescription use data for a prescribed drug identified in the single pharmacy claim record if it satisfies the criterion: no more than one refill at an interval less than two times the first prescription's days supply;

c) categorizing episodes with two pharmacy claim records as follows:
  (i) if the two pharmacy claim records indicate for a single drug prescription no more than one refill at an interval less than two times the prescription's days supply, and fall within six times the days supply added to the last fill for that prescription, then categorizing the two pharmacy claim records as a single AI episode,
  (ii) if one of the two claim records falls within six times the days supply added to the last fill date for that prescription and one claim record is greater than six times the days supply added to the last fill for that prescription, then categorizing the two pharmacy claim records as two separate AI episodes, and
  (iii) if an interval between an original and subsequent refill fill date for the two pharmacy claim records is three times or more than the days supply for an original prescription, then categorizing the two pharmacy claim records as an extended intervention (EI) episode;

d) categorizing the three or more pharmacy claim records sorted into the third group as follows: if the intervals between successive fill dates of the three or more pharmacy claim records are less than two times the days supply, then categorizing all the three or more pharmacy claim records as one maintenance episode (ME); and storing the one or more pharmacy episodes and the respective category in a data table for monitoring usage of a prescription drug identified in the pharmacy claim data records.

* * * * *